United States Patent [19]

Poe et al.

[11] 4,455,289

[45] Jun. 19, 1984

[54] COMBINED PROCESS FOR PREPARING ALUMINA AND ALPHA-OLEFINS

[75] Inventors: R. L. Poe; D. J. Royer, both of Ponca City, Okla.

[73] Assignee: Conoco Inc., Ponca City, Okla.

[21] Appl. No.: 405,973

[22] Filed: Aug. 6, 1982

[51] Int. Cl.$^3$ .......................... C01F 7/02; C07C 2/02; C07C 2/88

[52] U.S. Cl. .................................. 423/630; 585/528; 585/522; 585/637

[58] Field of Search ................ 423/630; 585/328, 522, 585/637

[56] References Cited

U.S. PATENT DOCUMENTS

| | | | |
|---|---|---|---|
| 3,278,262 | 10/1966 | Poe et al. | 585/527 |
| 3,423,444 | 1/1969 | Atwood | 585/328 |
| 3,445,494 | 5/1969 | Cecciani | 585/328 |

FOREIGN PATENT DOCUMENTS 844637  8/1960  United Kingdom ................ 423/630

Primary Examiner—Herbert T. Carter
Attorney, Agent, or Firm—Robin M. Davis

[57] ABSTRACT

A combined process for preparing alumina and alpha-olefins (α-olefins) is disclosed. The process comprises:
(a) reacting tri-($C_2$ to $C_{24}$) alkylaluminum with ethylene in the presence of nickel catalyst to form triethylaluminum and $C_2$ to $C_{24}$ α-olefins,
(b) adding aluminum tri-($C_4$ to $C_8$) alcoholate to the reaction product of step (a),
(c) equilibrating the admixture of step (b) so that substantially all of the triethylaluminum is converted into aluminum ethyl alcoholates, compounds with at least one $C_4$ to $C_8$ alcoholate group per molecule,
(d) subjecting the equilibrated mixture of step (c) to a fractionation to recover, (1) a $C_2$ to $C_{24}$ α-olefin fraction, and (2) an aluminum ethyl alcoholate fraction (a mixture of compounds with the general formula $Al(C_2H_5)_X(OC_6H_{13})_Y$ (where X is 0 to 2 and Y is 3 to 1) and $X+Y=3$).
(e) adding $C_4$ to $C_8$ alcohol to the aluminum ethyl alcoholate fraction to form aluminum tri-($C_4$ to $C_8$) alcoholate and ethane,
(f) separating the ethane and aluminum tri-($C_4$ to $C_8$) alcoholate by fractionation, and
(g) hydrolyzing the aluminum tri-($C_4$ to $C_8$) alcoholate to form $C_4$ to $C_8$ alcohols and the desired alumina, and process being characterized further in that preferably the tri-($C_2$ to $C_{24}$) alkylaluminum is prepared by:
(1) preparing triethylaluminum from aluminum, ethylene and hydrogen, in two stages, and
(2) reacting with triethylaluminum of step (1) with ethylene to form tri-($C_2$ to $C_{24}$) alkylaluminum.

8 Claims, 1 Drawing Figure

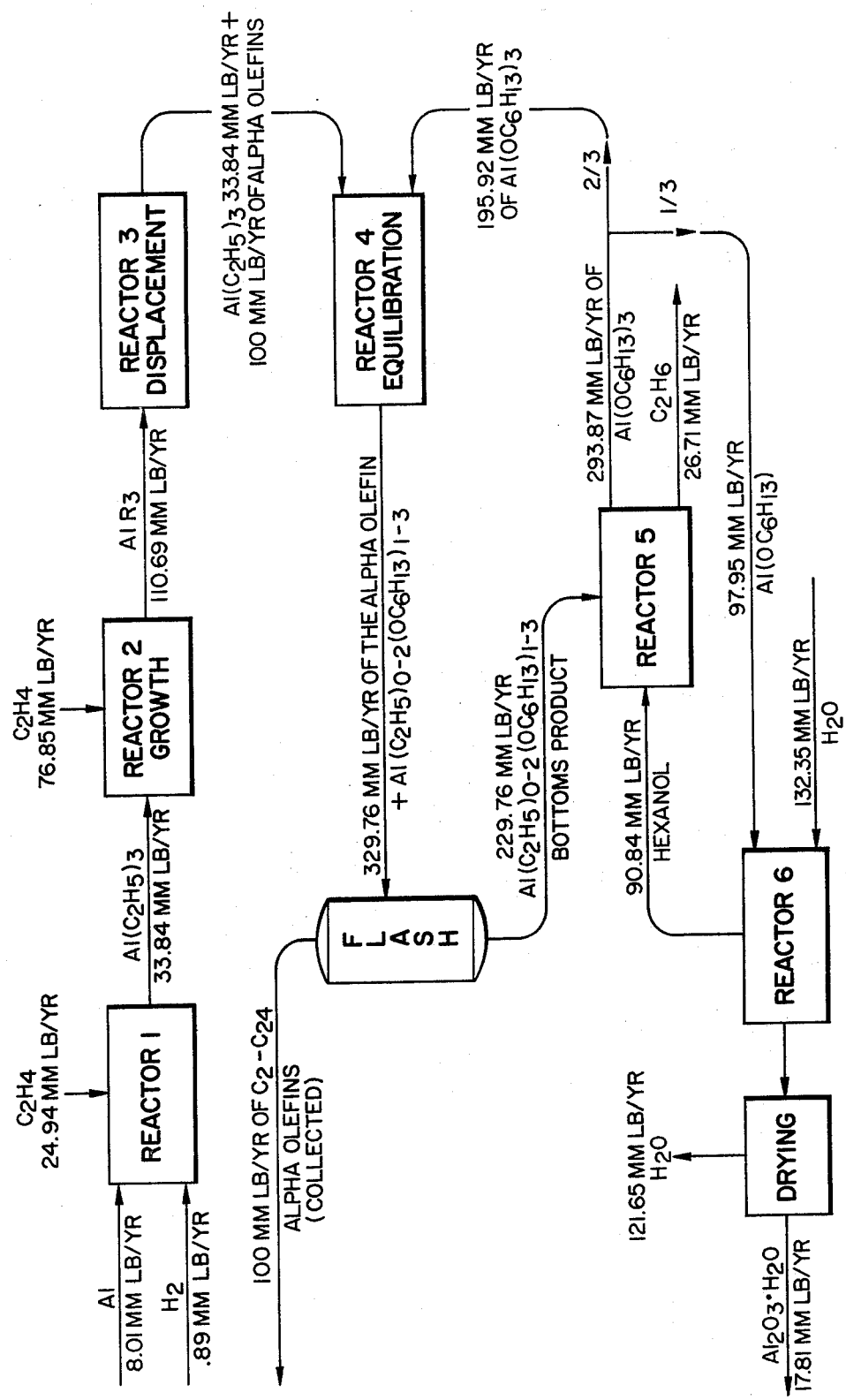

COMBINED PROCESS FOR PREPARING ALUMINA AND ALPHA-OLEFINS

BACKGROUND OF THE INVENTION

1. Field of the Invention

The invention is in the general field of combined processes for preparing alpha-olefins and alumina from a "growth product" comprising substantially tri-$C_2$-$C_{24}$ alkylaluminum. More specifically, the invention deals with a process for making both alumina and alpha-olefins including a step which calls for the equilibration of alpha-olefins, triethylaluminum, and aluminum trialcoholate (the alcoholate portions having from 4 to 8 carbon atoms).

2. General Background

It is well-known how to prepare triethylaluminum ($Al(C_2H_5)_3$) from aluminum, (Al) ethylene ($C_2H_4$) and hydrogen ($H_2$). The details of this preparation will be discussed in the detailed description). It is well-known that triethylaluminum ($Al(C_2H_5)_3$) will react with ethylene ($C_2H_4$) to produce an aluminum product in which the alkyl substituents have increased in length by multiples corresponding to the number of moles of ethylene which have been added between the aluminum and the ethyl groups. The resulting product is usually referred to as "growth product". The "growth product" can be used for the production of other useful materials such as high molecular weight alcohols and alpha-olefins ($\alpha$-olefins).

The preparation of alpha-olefins from "growth product" is accomplished by a further reaction of growth with ethylene, (this reaction is known as a displacement reaction). This can be done by any of several methods. One preferred method is to conduct the displacement reaction in the presence of a reduction catalyst such as nickel. Conducting the reaction in the presence of a nickel catalyst has the advantage that it can be conducted at low temperatures and pressures and still obtain a resulting high conversion.

The displacement reaction conducted in the presence of nickel has the following disadvantage. During the separation of the high molecular weight olefins from the low molecular weight aluminum trialkyls ($Al(R)_3$) the reaction product tends to undergo reverse displacement and the high molecular weight olefins tend to isomerize and dimerize under the conditions required for distillation.

The use of an aluminum complexing agent is known in the art and is exemplified in U.S. Pat. No. 3,278,262 which employs an alkali metal cyanide-aluminum alkyl complex to produce both olefins and alkanols. In this process after destruction of the aluminum complex hydrolysis is used to produce hydrated alumina. The hydrolysis also converts alkoxides to alkanols.

We have discovered that adding an aluminum tri-$C_4$ to -$C_8$ alcoholate (the alcoholate portions having from 4 to 8 carbon atoms per alcoholate group) to the displacement reaction product, prior to fractionation, prevents deleterious side reactions, e.g. reverse displacement and olefin isomerization. We have furthermore eliminated the necessity of using cyanide, which is poisonous, and difficult to dispose of.

BRIEF SUMMARY OF THE INVENTION

Briefly stated, the present invention is directed to a combined process for preparing alumina ($Al_2O_3.H_2O$) and $\alpha$-olefins comprising:

(a) reacting trialkylaluminum compounds, having alkyl groups in the range from 2 to about 24 carbon atoms, with ethylene in the presence of a reduction catalyst, to form triethylaluminum, and alpha-olefins in the range of from 2 to about 24 carbon atoms, (b) adding aluminum tri-alcholoates, where the alcoholate portion contains from 4 to 8 carbon atoms, to the reaction product of step (a), (c) equilibrating the admixture of step (b) such that substantially all of the triethylaluminum is converted into compounds with at least one $C_{4\ to\ 8}$ alcoholate group per molecule, (compounds with the general formula $Al(C_2H_5)_X(OC_{4\ to\ 8}H_{9\ to\ 17})_Y$ where X=0 to 2, Y=3 to 1 and X+Y=3), (d) subjecting the equilibrated mixture of step (c) to a fractionation to recover (1) an alpha-olefin fraction in the range having from 2 to 24 carbon atoms per molecule, and (2) an aluminum ethyl alcoholate bottoms fraction (a mixture of compounds having the general formula $Al(C_2H_5)_X(OC_{4\ to\ 8}H_{9\ to\ 17})_Y$ where X=0 to 2, Y=3 to 1 and X+Y=3, (e) adding alcohol in the ranges having from 4 to 8 carbon atoms per molecule, to the aluminum ethylalcoholate bottoms fraction to form aluminum tri-alcoholate containing from 4 to 8 carbon atoms per alcoholate portion, and ethane, (f) separating the ethane and aluminum trialcoholate products from step (e), and, (g) hydrolyzing the aluminum trialcoholates from step (e) to form alumina, and alcohols containing from 4 to 8 carbon atoms per molecule.

In a preferred embodiment the tri-$C_2$ to $C_{24}$-alkylaluminum is prepared by a process including steps:

(a) preparing a triethylaluminum from aluminum, ethylene and hydrogen, in two stages and (b) reacting the triethylaluminum of step (a) with ethylene to form tri-$C_2$ to $C_{24}$ alkylaluminum.

DETAILED DESCRIPTION

Preparation of Triethylaluminum

The triethylaluminum ($Al(C_2H_5)_3$) is prepared in two stages the operating sequence of which can be illustrated by the following reactions:

$$Al + 3/2 H_2 + 2Al(C_2H_5)_3 \rightarrow 3Al(C_2H_5)_2H \quad (a)$$

$$3Al(C_2H_5)_2H + 3C_2H_4 \rightarrow 3Al(C_2H_5)_3 \quad (b)$$

The overall effect of the two reactions is to produce three moles of triethylaluminum for each two moles of triethylaluminum initially present. Basically, then, the combined effect of the two reactions is to prepare triethylaluminum from aluminum, ethylene and hydrogen.

In preparing the diethylaluminum hydride an "active" aluminum is used. (By "active" aluminum is meant one which has a relatively fast reaction rate.) One means of preparing an "active" aluminum is disclosed in U.S. Pat. No. 3,104,252 wherein an aluminum alloy, containing intentionally added amounts of titanium or zirconium, is used. It is to be understood that any active aluminum can be used.

The process conditions for preparing the diethylaluminum hydrides are disclosed in U.S. Pat. No. 3,104,252, which patent is made a part of this disclosure.

The reaction conditions for reacting the diethylaluminum hydride with ethylene are well-known in the art. Typically, these conditions are:

|  | Suitable | Preferred |
| --- | --- | --- |
| Temperature (°C.) | 60–180 | 120–180 |
| Pressure (psig) | 10–800 | 300–600 |
| Res. Time (min) (Residence) | 5–90 | 10–30 |

Growth Reaction

The reaction of additional ethylene with the triethylaluminum to form tri-$C_2$ to $C_{24}$ alkylaluminum is referred to as a "growth reaction". The product of this reaction has a Poisson distribution as described in U.S. Pat. No. 3,445,494, which patent is made a part of this disclosure.

The growth reaction is typically conducted under the following conditions.

|  | Suitable | Preferred |
| --- | --- | --- |
| Temperature (°C.) | 80–160 | 110–130 |
| Press. (psig) | 500–2500 | 1200–1800 |
| Res Time (min) (Residence) | 30–240 | 120–150 |

Displacement Reaction

The reaction of the tri-$C_2$ to $C_{24}$-alkylaluminum with ethylene to form triethylaluminum and α-olefins is referred to as a displacement reaction. While there are many ways of conducting the displacement reaction our invention is restricted to processes wherein nickel or other reduction catalysts, e.g. cobalt, palladium or iron are used in the reaction. In these reactions, the preferred catalyst is nickel.

The nickel can be present as finely divided metallic nickel, Raney nickel, nickel acetyl-acetonate, nickel napthenate, etc. An effective amount of catalyst is usually in the range of about 0.001 to about 0.1 weight percent based on the tri-$C_2$ to $C_{24}$ alkylaluminum.

Generally, the reaction is conducted employing about 200 to about 1,000 mole percent ethylene per mole of tri-$C_2$ to $C_{24}$ alkylaluminum. The presence of ethylene at a minumum pressure of 50 pounds per square gauge (psig) will tend to prevent isomerization and reverse displacement until the equilibration step is completed. Acceptable ranges for the conditions of the reaction permit temperatures in the range of about 10° to about 200° C., preferably about 60° to about 100° C., and pressures from about 50 to about 800 psig, preferably about 100 to about 300 psig.

If desired, a solvent may be used. The solvent should be one that is readily separable from the recovered olefins. Heptane or nonane, for example, would be appropriate.

Equilibration With Aluminum Trialcoholate and Recovery Of Alpha-Olefin

Following displacement, while still under a pressure of about 50 psig ethylene, aluminum trialcoholate, having from 4 to 8 carbon atoms per alcoholate group, is combined with the displacement reaction products, (i.e., the alpha-olefins, and the $Al(C_2H_5)_3$). The preferred aluminum alcoholate is aluminum trihexanolate. However, any alcohol in the range of $C_4$ to $C_8$ can be used. Use of an alcoholate from a $C_4$ alcohol results in a large amount of water in the alcohol phase during alumina preparation. Use of an aluminum alcoholate from a $C_8$ alcohol results in a high boiling point alcoholate which requires a larger amount of energy in the process. It is apparent that alcohols outside the $C_4$ to $C_8$ range can be used, but are not practical in our process. Preferable alcohols in this range are the even numbered carbon atom alcohols, $C_4$, $C_6$, $C_8$, alcohol. Of these, the most preferable is the $C_6$ alcohol.

The resulting admixture, (the displacement reaction products and aluminum tri-$C_4$ to $C_8$ alcoholate) is equilibrated so that each aluminum atom has at least one alcoholate group attached to it. Thus the $Al(C_2H_5)_3$ is substantially all converted to compounds having the general formula $Al(C_2H_5)_X(OC_{4\ to\ 8}H_{9\ to\ 17})_Y$ where X may be from 0 to 2 and Y may be from 3 to 1 so that X+Y equals 3. The amount of aluminum trialcoholate added should be at least sufficient to accomplish this. Acceptable ranges for the conditions during equilibration are:

|  | Suitable | Preferred |
| --- | --- | --- |
| Pressure | 50 to 800 psig | 100 to 300 |
| Temp | 10° C. to 200° C. | 60° to 100° C. |

Since the $Al(C_2H_5)_3$ has been substantially eliminated, problems of isomerization and reverse displacement, which decrease the alpha-olefin concentration, are avoided.

The mixture of alpha-olefins and the aluminum alkylalcoholate, compounds with the general formula $Al(C_2H_5)_{X=0\ to\ 2}(OC_{4\ to\ 8}H_{9\ to\ 17})_{Y=3\ to\ 1}$ is then fractionated so that the $C_2$ to $C_{24}$ alpha-olefins are removed. If desired, the $C_2$ olefin (ethylene) may be separated and used to form the triethylaluminum; the diethylaluminum hydride, or in the displacement reaction to displace the alkyl group. The bottoms product is the aluminum alkyl alcoholate compounds mixture.

Formation And Recovery Of Aluminum Trialcoholates

The bottoms product from the fractionation is combined with a $C_4$ to $C_8$ alcohol to convert the aluminum alkylalcoholates to substantially all aluminum tri-$C_4$ to $C_8$ alcoholate and ethane. The amount of alcohol is at least sufficient to convert the aluminum ethylate to aluminum trialcoholate ($Al(OC_{4\ to\ 8}H_{9\ to\ 17})_3$).

The ethane is removed from the admixture by simple distillation. It can be recovered and sent to an ethylene plant, or could be burned or injected into a natural gas line.

It should be noted at this point that the aluminum trialcoholate $[Al(OC_{4-8}H_{9-17})_3]$ (aluminum trialcoholate where the alcoholate portion has from 4 to 8 carbon atoms per molecule) may be used in two distinct manners. It may be hydrolyzed, as described in the next step, or it may be used in the equilibration reaction with the triethylaluminum. Since a key portion of our invention involves the elimination of substantially all of the triethylaluminum before removal of the alpha-olefins, a more preferred method is to divide the aluminum tri-$C_4$ to 8 alcoholate into two portions. One portion will be hydrolyzed to produce alumina, ($Al_2O_3.H_2O$) and the other will be added to the product from the displacement reaction so that equilibration may take place.

Hydrolysis Of Aluminum Trialcoholates

The aluminum trialcoholates can be converted to alumina by hydrolysis using any of several known techniques. The conventional method employed in this case is substantially the method depicted in U.S. Pat. No. 3,419,352 which patent is made a part of this disclosure.

The following example is presented to illustrate the present invention and not to limit it. In the example, all parts and percentages are by weight unless otherwise specified. A figurative depiction of this embodiment is provided for clarification. The accompanying figure depicts a preferred embodiment of this process. The reactions must be carried out in the stated order, but both reaction vessels and quantities of materials used may vary. It may be desirable, for example, to use one vessel for several of the reactions. Another variable is the use made of the $C_2$ olefin product, and of the $H_2O$ given off by drying. Either of these may be recycled into the process when and where there is a need for ethylene or $H_2O$ respectively.

For clarity and convenience the amounts of reactants and products used in the example are shown on the figure illustrating the process.

EXAMPLE-DISCUSSION-EXPLANATION

MMlb/yr = million lb/yr.

EXAMPLE 8.01 MMlb/yr of activated aluminum (Al) 0.89 MMlb/yr of $H_2$ and 24.94 MMlb/yr of ethylene are combined in reactor 1 (the unit for making triethylaluminum ($Al(C_2H_5)_3$).

The overall reaction takes place in two stages. The first stage is at about 138° C. temperature and 1200 psig pressure. The aluminum used has been activated in the presence of titanium. After the production of diethylaluminum hydride ($Al(C_2H_5)_2H$) in the first stage, which uses the activated Al, $H_2$, and some $Al(C_2H_5)_3$, the second stage takes place. About 24.94 MMlb/yr. of ethylene ($C_2H_4$) at 500 psig, and at about 150° C., react with the $Al(C_2H_5)_2H$, and produces 33.84 MMlb/yr $Al(C_2H_5)_3$ which is used in the growth reaction.

Approximately 33.84 MMlb/yr of $Al(C_2H_5)_3$ from reactor 1, and 76.85 MMlb/yr of ($C_2H_4$) is combined in reactor 2, (the growth reaction unit), at about 120° C. and 1600 psig so that the alkyl aluminum growth product $AlR_3$ is formed. Approximately 110.69 MMlb/yr of $AlR_3$ is produced, and is combined with 23.15 MMlb/yr of $C_2H_4$ and 0.001-0.1 weight percent of Ni catalyst in reactor 3, where the displacement reaction is conducted. The temperature is maintained at about 80° C. and pressure is at about 200 psig. The displacement reaction takes place so that approximately 100 MMlb/yr of alpha-olefins and 33.84 MMlb/yr of $Al(C_2H_5)_3$ is formed. These displacement products are then put into reactor 4 where equilibration takes place.

195.92 MMlb/yr of aluminum trihexonolate ($Al(OC_6H_{13})_3$ is added to reactor 4 under 50 psig pressure. The admixture is permitted to equilibrate under this pressure while temperatures are maintained in the range of 60° to 100° C. After this, the resulting mixture of $Al(C_2H_5)_{0-2}(OC_6H_{13})_{1-3}$ compounds, and alpha-olefins are fed into the fractionation tower, where the alpha-olefins are removed.

About 229.76 MMlb/yr of bottoms product, a mixture of compounds having the general formula $Al(C_2H_5)_X(OC_6H_{13})_Y$ (where $X=0-2$ and $Y=3-1$ and $X+Y=3$) is recovered. This is put into reactor 5 with about 90.84 MMlb/yr of hexanol under atmospheric pressure and at about 100° C. where the mixture of $Al(C_2H_5)_X(OC_6H_{13})_Y$ (where $Y=1-3$ and $X=2-0$ and $X+Y=3$) compounds are converted to 293.87 MMlb/yr of ($Al(OC_6H_{13})_3$ and 26.71 MMlb/yr of ethane ($C_2H_6$).

After taking off 26.71 MMlb/yr of $C_2H_6$ in a distillation, 97.95 MMlb/yr of $Al(OC_6H_{13})_3$ is combined in reactor 6 with 132.35 MMlb/yr of $H_2O$. (Note that the water is then present in excess.) The rest of the $Al(OC_6H_{13})_3$, approximately 195.92 lb/yr, is recycled and combined with the displacement product for equilibration before distillation of the olefins. In hydrolysis, the following reaction takes place. $Al(OC_6H_{13})_3 + \text{excess } H_2O \rightarrow \frac{1}{2}Al_2O_3.H_2O + 3C_6H_{13}OH$. Hydrolysis takes place under temperatures maintained in the range of 70° to 95° C. and at atmospheric pressure.

After drying, approximately 121.65 MMlb/yr of $H_2O$ are removed, 17.81 MMlb/yr of $Al_2O_3.H_2O$ is formed. The 90.84 MMlb/yr of hexanol ($C_6H_{13}OH$) are recycled into reactor 5 with the $Al(C_2H_5)_X(OC_6H_{13})_Y$ ($Y=3-1$, $X=0-2$, and $X+Y=3$) compounds.

While certain details have been shown for the purposes of illustrating this invention, it will be apparent to those skilled in this art that various changes and modifications may be made herein, without departing from the script or scope of the invention.

Thus, having described our invention, what we claim and desire to secure by Letters Patent are:

1. A combined process for the preparation of alumina and alpha-olefins comprising:
   (a) reacting trialkylaluminum compounds having alkyl groups in the range of from 2 to about 24 carbon atoms with ethylene at temperatures in the range of from about 10° C. to about 200° C., and at pressures of from about 50 to about 800 psig in the presence of a reduction catalyst selected from the group consisting of cobalt, palladium, iron, nickel, or a reducing nickel compound selected from the group consisting of Raney nickel, nickel acetylacetonate, and nickel napthenate to form triethylaluminum and alpha-olefins in the range of from 2 to about 24 carbon atoms,
   (b) adding aluminum trialcoholates, where the alcoholate portion contains from 4 to 8 carbon atoms, to the reaction product of step (a),
   (c) allowing the admixture of step (b) to react at pressures in the range of from about 50 to about 800 psig, and at temperatures in the range of from about 10° to about 200° C., whereby substantially all of the triethylaluminum is converted into compounds with at least one $C_{4 \text{ to } 8}$ alcoholate group per molecule, wherein said compounds have the general formula $Al(C_2H_5)_X(OC_{4 \text{ to } 8}H_{9 \text{ to } 17})_Y$ where $X=0$ to 2, $Y=3$ to 1 and $X+Y=3$,
   (d) fractionating the mixture resulting after completion of step (c) to recover (1) an alpha-olefin fraction in the range having from 2 to 24 carbon atoms per molecule, and (2) an aluminum ethyl alcoholate bottoms fraction (a mixture of compounds having the general formula $Al(C_2H_5)_X(OC_{4 \text{ to } 8}H_{9 \text{ to } 17})_Y$ where $X=0$ to 2, $Y=3$ to 1 and $X+Y=3$),
   (e) adding alcohol in the ranges having from 4 to 8 carbon atoms per molecule, to the aluminum ethylalcoholate bottoms fraction to form aluminum trialcoholate containing from 4 to 8 carbom atoms per alcoholate portion, and ethane, (f) separating the ethane and aluminum trialcoholate products from step (e), and, (g) hydrolyzing the aluminum trialcoholates from step (e) to form alumina and alcohols containing from 4 to 8 carbon atoms per molecule.

2. A combined process for preparing alumina and alpha-olefins as described in claim 1, said process being further characterized by an initial step whereby:

the tri-alkyl aluminum compounds of step (a) containing alkyl groups in the range having from 2 to 24 carbon atoms are formed by reacting triethylaluminum with ethylene.

3. A combined process for preparing alumina and alpha-olefins as described in claim 2, said process being further characterized by an initial step whereby:

the triethylaluminum is formed in two stages using aluminum, hydrogen and ethylene.

4. A combined process for preparing alumina and alpha-olefins as described in claim 3, wherein:

the reduction catalyst used in (a) to displace the alkyl group is a nickel catalyst.

5. A combined process for preparing alumina and alpha-olefins as described in claim 4, wherein:

the alcohols produced by the hydrolysis of step (g) are added to the aluminum ethyl alcoholate fraction in step (e).

6. A combined process for preparing alumina and alpha-olefins as described in claim 5 wherein:

a portion of the aluminum trialcoholate separated from the ethane in step (f) is added in step (b) to the alpha-olefin and triethylaluminum reaction product.

7. A combined process as described in claim 6 wherein:

the alcohol and the alcoholate compounds have alcoholate units containing six carbon atoms.

8. A combined process as described in claim 7 wherein:

$C_2$ olefin (ethylene) is separated from the alpha-olefin fraction of step (d), and wherein the separated $C_2$ olefin (ethylene) is then used in the formation of triethylaluminum, or in (a) to displace the alkyl group.

* * * * *